United States Patent [19]

Fecondini et al.

[11] Patent Number: 5,045,207
[45] Date of Patent: Sep. 3, 1991

[54] MULTI-CONCENTRATION DISPOSABLE LIQUID CONCENTRATING DEVICE

[76] Inventors: Luciano Fecondini, Via Borgo San Pietro 134,, 1-40126 Bologna, Italy; Enzo Vassarotti, Villa Charbon, CH-1172 Bougy-Villars, Switzerland

[21] Appl. No.: 491,912

[22] Filed: Mar. 12, 1990

[30] Foreign Application Priority Data

Nov. 9, 1989 [IT] Italy .................................. 22328 A/89

[51] Int. Cl.$^5$ ...................... B01D 61/14; B01D 61/18
[52] U.S. Cl. .................................. 210/645; 210/652; 210/321.75; 210/321.84
[58] Field of Search ...................... 210/650, 321.6, 634, 210/644–647, 649, 651, 500.21, 500.27, 321.75, 321.84

[56] References Cited

U.S. PATENT DOCUMENTS

| | | | |
|---|---|---|---|
| 3,783,127 | 1/1974 | Cook et al. ............................. | 210/22 |
| 3,817,379 | 6/1974 | Zipilvian et al. ...................... | 210/94 |
| 4,082,668 | 4/1978 | Zeinch et al. ......................... | 210/129 |
| 4,632,761 | 12/1986 | Bowers et al. ........................ | 210/650 |

*Primary Examiner*—Frank Sever
*Attorney, Agent, or Firm*—Celia H. Ketley; William L. Baker

[57] ABSTRACT

A device for concentrating solute-containing solutions, e.g. macromolecular sample solutions, by filtration through a semipermeable membrane, which device enables the user to obtain various different retentate concentrations by placing the device in different positions before use. The device preferably comprises one or more concentration units, each said concentration unit comprising one or more chambers, each chamber having at least one wall impermeable to sample solution and at least one wall, in opposing spaced relation to said sample solution impermeable wall, formed of a semipermeable membrane permeable to said solvent and impermeable to the macromolecules or other solutes to be retained, said membrane having at least two regions of different area which regions are impermeable to said solvent, each of said regions providing a deadstop preventing filtration to dryness of the solvent through the membrane and providing a different final retentate concentration; and means for drawing said solvent through the membrane.

43 Claims, 3 Drawing Sheets

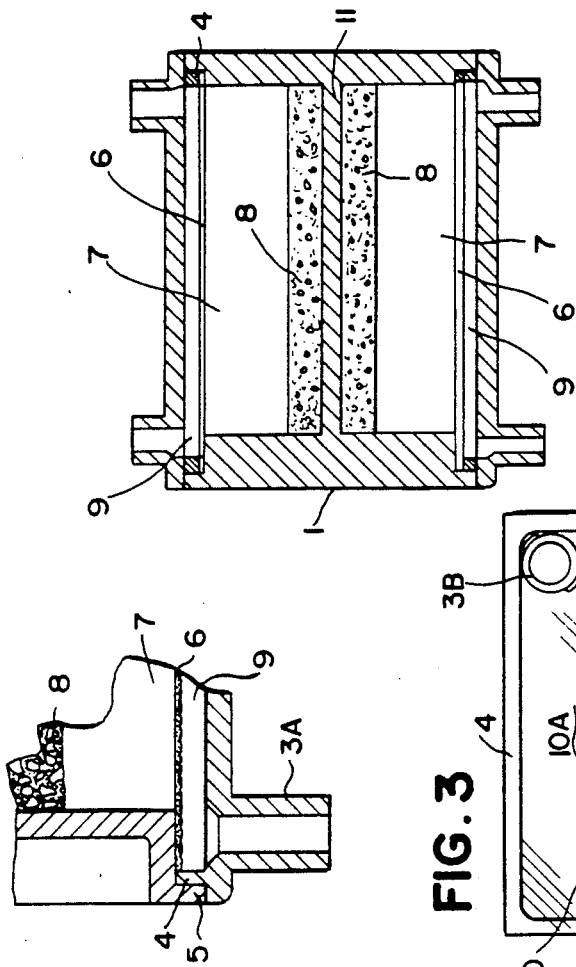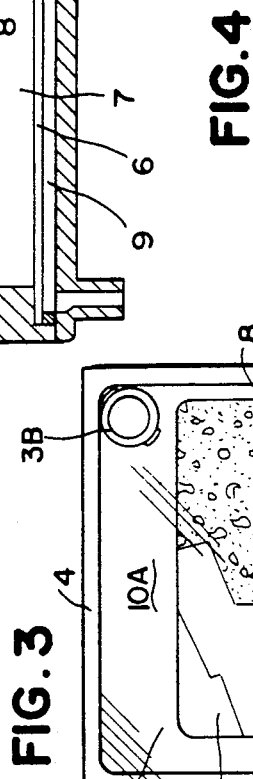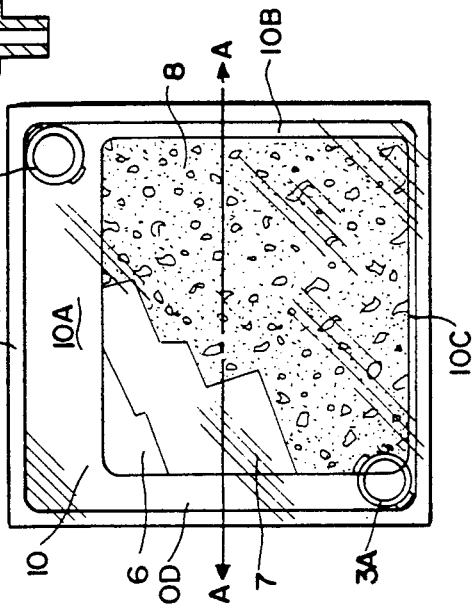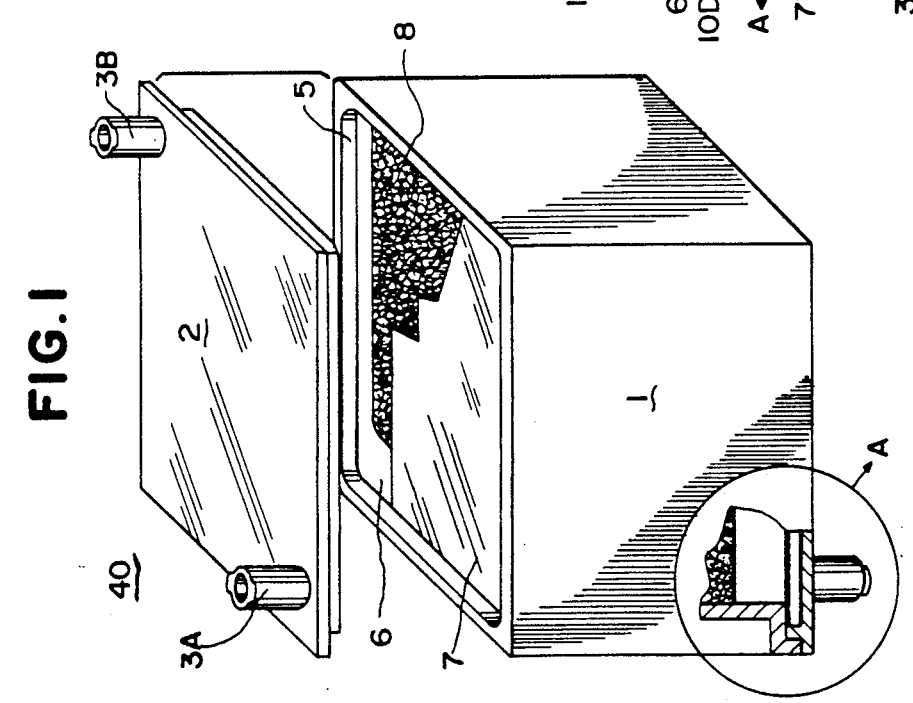

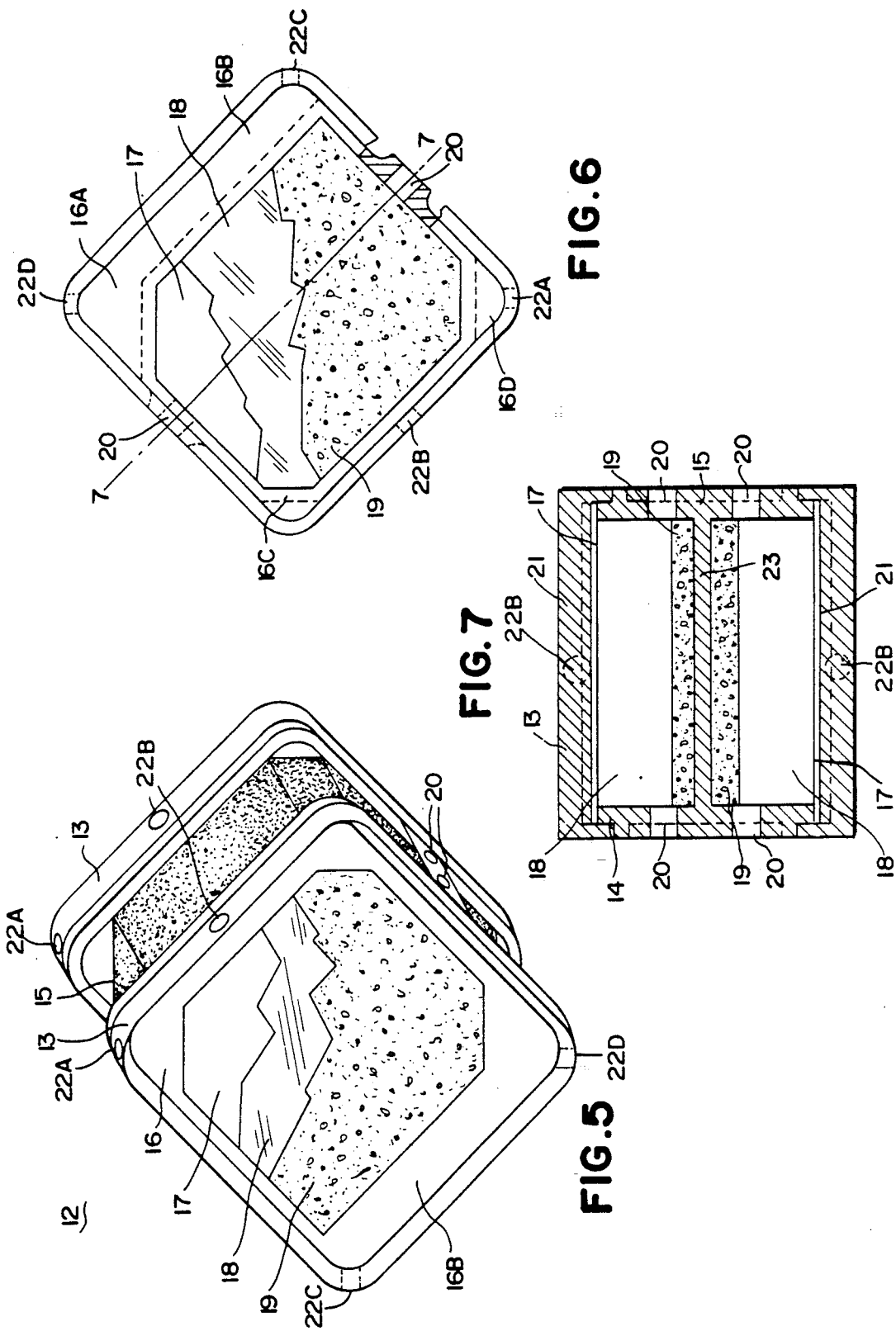

MULTI-CONCENTRATION DISPOSABLE LIQUID CONCENTRATING DEVICE

BACKGROUND OF THE INVENTION

This invention relates to a device for concentrating solute-containing solutions, e.g. solvent-containing macromolecular sample solutions, via filtration through a semipermeable membrane, and more particularly to a device which enables the user to obtain various desired retentate concentrations by placing the device in different positions before use. The device of the invention provides rapid concentration of liquid analytical specimens without filtering to dryness.

Effective use of modern analytical techniques for rapid analysis of liquid specimens, particularly biological specimens such as plasma, whole blood, cerebrospinal fluid, or urine, generally requires a small volume of a sample solution which has a concentration of macromolecules which is substantially greater than that of the naturally occurring liquid specimen. Previously, dialysis or ultrafiltration devices such as those described in U.S. Pat. Nos. 3,488,768 and 3,565,256 were used to obtain such sample solutions. However, these devices required expensive auxiliary equipment to induce flow through the membrane, and necessitated the cleaning of the sample chamber after each use.

These difficulties were overcome by the microconcentrator described in U.S. Pat. No. 3,817,379, the disclosure of which is incorporated herein by reference. This microconcentrator is inexpensive and hence disposable, and is capable of providing rapid concentration of samples in short periods of time. This microconcentrator is provided with an impermeable seal coating on the portion of the membrane in contact with the desired final retentate volume. It appears that this coating greatly impedes filtration to dryness, but does not prevent it altogether, due to wicking by surface tension forces, which allows continued filtration after the retentate meniscus recedes onto the coated area. When concentrating small volumes of macromolecules in solution using filtration, e.g. ultrafiltration, there exists the problem of filtration to dryness. Although a fixed volume of buffer may be added to a microvolume concentration device to redissolve macromolecules retained after filtration to dryness, it is generally found that total mass recovery of macromolecules is significantly less, and biological activity recovery is often reduced, as compared to the case when filtration is stopped at the desired final retentate volume. Furthermore, one is unable to obtain various different retentate concentrations using this microconcentrator, unless one uses a method such as having th operator monitor the concentration and withdraw the concentrated sample before filtration stops, using a different microconcentrator for each different retentate concentration desired, etc. These procedures tend to increase the possibility of operator error, and may be uneconomical.

As with the devices of the present invention, the microconcentrator described in U.S. Pat. No. 4,632,761, the disclosure of which is incorporated herein by reference, has a means for preventing filtration to dryness (a "deadstop"). In this microconcentrator device, the filtrate duct or ducts of the membrane support are offset sufficiently inward from the edge of the membrane to enable filtration to stop and a concentrated macromolecular final retentate volume to be obtained when the apparatus is used in a centrifuge rotor and the retentate meniscus reaches the centrifugal radial level of the outermost edge of the outermost filtrate duct. This microconcentrator, unlike the microconcentrator of the invention, requires the use of a centrifuge. Final retentate volume may be varied using the same microconcentrator by selection of centrifuge rotors of differing angles or by variation of the axial alignment of the apparatus in the fixed angle rotor, assuming the filtrate ducts are asymmetric. In the latter case, however, in order to axially align the apparatus in the fixed angle rotor, means, such as a tab positioned on the edge of the membrane support, is required.

Accordingly, it is a principal object of this invention to provide a simple microconcentrator which enables the user to obtain many differing, precisely controlled, retentate concentrations.

It is another object of this invention to provide such a microconcentrator which can concentrate macromolecules or other solutes from a solution without filtering to dryness.

It is a further object of this invention to provide such a microconcentrator that is disposable.

It is a still further object of the invention to provide such a microconcentrator that is economical to manufacture.

SUMMARY OF THE INVENTION

The present invention relates to a device for concentrating liquid solutions containing macromolecules or other solutes by filtration, e.g. ultrafiltration, through a semipermeable membrane, and more particularly to a device which enables the user to obtain different desired retentate concentrations by placing the device in different positions before use.

The present invention provides a device for removing solvent from a solute-containing solution, e.g. a solvent-containing macromolecular sample solution, to obtain a desired final retentate concentration. The term solute-containing solution ("solution") as used herein includes macromolecular solutions, which are generallyconcentrated by ultrafiltration, as well as solutions containing other solutes such as bacteria, cell debris and viruses, wich are generally concentrated by microfiltration, etc. The device of the invention comprises at least one concentration unit, each said concentration unit comprising one or more chambers, each chamber having at least one chamber wall impermeable to sample solution and at least one wall, in opposing spaced relation to said chamber wall, formed of a semipermeable membrane permeable to said solvent and impermeable to the solute to be retained, said membrane having at least two regions of different area, which regions are impermeable to said solvent, each of said regions providing a means for preventing filtration to dryness of the solvent through the membrane (a "deadstop") and providing a different final retentate concentration; and means for drawing said solvent through said membrane. Preferably, the chamber further comprises side walls which support the membrane in opposing spaced relation to the chamber wall. The device preferably further comprises means for introducing sample solution to the chamber and for removing concentrated liquid retentate from the chamber.

In a preferred embodiment of the invention, the means for drawing solvent through the membrane comprises at least one absorbent layer disposed closely adjacent the side of the membrane furthest from the chamber and preferably further comprises means for providing apposition between said membrane and its adjacent absorbent layer. This apposition providing means preferably comprises a layer of resilient material disposed adjacent the absorbent layer and preferably further comprises means for retaining the resilient layer adjacent the absorbent layer, wherein said retaining means serves to compress the resilient layer such that the absorbent layer is pressed against the membrane. In this embodiment, each said resilient layer and adjacent absorbent layer is preferably surrounded on each face, except the face of the absorbent layer adjacent to the membrane, by solvent impermeable walls which form a retaining compartment for the absorbent and resilient layers. In an alternate embodiment, apposition may be provided without a resilient layer simply by utilizing a compressible absorbent layer and compressing said absorbent layer.

In another embodiment, the device may comprise, instead of the resilient and absorbent layers, simply a membrane support and vacuum means to draw the solvent through the membrane.

The device of the invention preferably comprises an enclosure for the at least one concentration unit, said enclosure being impermeable to the sample solution. The device preferably further comprises two concentration units which have their membrane walls in opposing spaced relation, and have at least one wall impermeable to the sample solution separating the concentration units.

In a further embodiment of the invention, the solvent impermeable membrane regions having different areas have substantially rectangular shape and extend lengthwise along the periphery of the membrane, which in this embodiment is preferably square or rectangular.

In an alternate embodiment of the invention, the membrane is again square or rectangular, and there are either four approximately triangular solvent impermeable membrane regions having different areas, one at each corner of the membrane, or three approximately triangular solvent impermeable membrane regions at three corners of the membrane and one approximately rectangular solvent impermeable membrane region which extends along one side of the membrane at the periphery of the membrane. Preferably the resilient layer and absorbent layer have approximately the same length and width, and are shaped to correspond to the portion of the membrane which is permeable to solvent.

In its method aspects the present invention is directed to a method of obtaining a final retentate having a desired concentration comprising the steps of: 1) introducing a solution to be concentrated, e.g. a macromolecular sample solution, to the chamber of the device; and 2) obtaining a predetermined quantity of solute concentrated liquid retentate, e.g. concentrated macromolecular liquid retentate, by drawing solvent through the membrane until the liquid level in the chamber is at the upper margin of one of the solvent impermeable membrane regions and filtration stops. It is not necessary to withdraw the concentrated retentate immediately after concentration, as the device will not filter to dryness.

The device thus provided allows the user to obtain different retentate concentrations simply by changing the position of the device.

BRIEF DESCRIPTION OF THE DRAWINGS

FIG. 1 is a partly exploded, partly broken away perspective view of one embodiment of the device.

FIG. 2 is an enlarged view of detail A in FIG. 1.

FIG. 3 is a partly broken away front planar view of the device of FIG. 1.

FIG. 4 is a vertical section taken across line A—A of FIG. 3.

FIG. 5 is a partly broken away perspective view of a preferred embodiment of the device.

FIG. 6 is a partly broken away front planar view of the device of FIG. 5.

FIG. 7 is a vertical section taken across line A—A of FIG. 6.

DETAILED DESCRIPTION OF THE INVENTION

Figure 8:
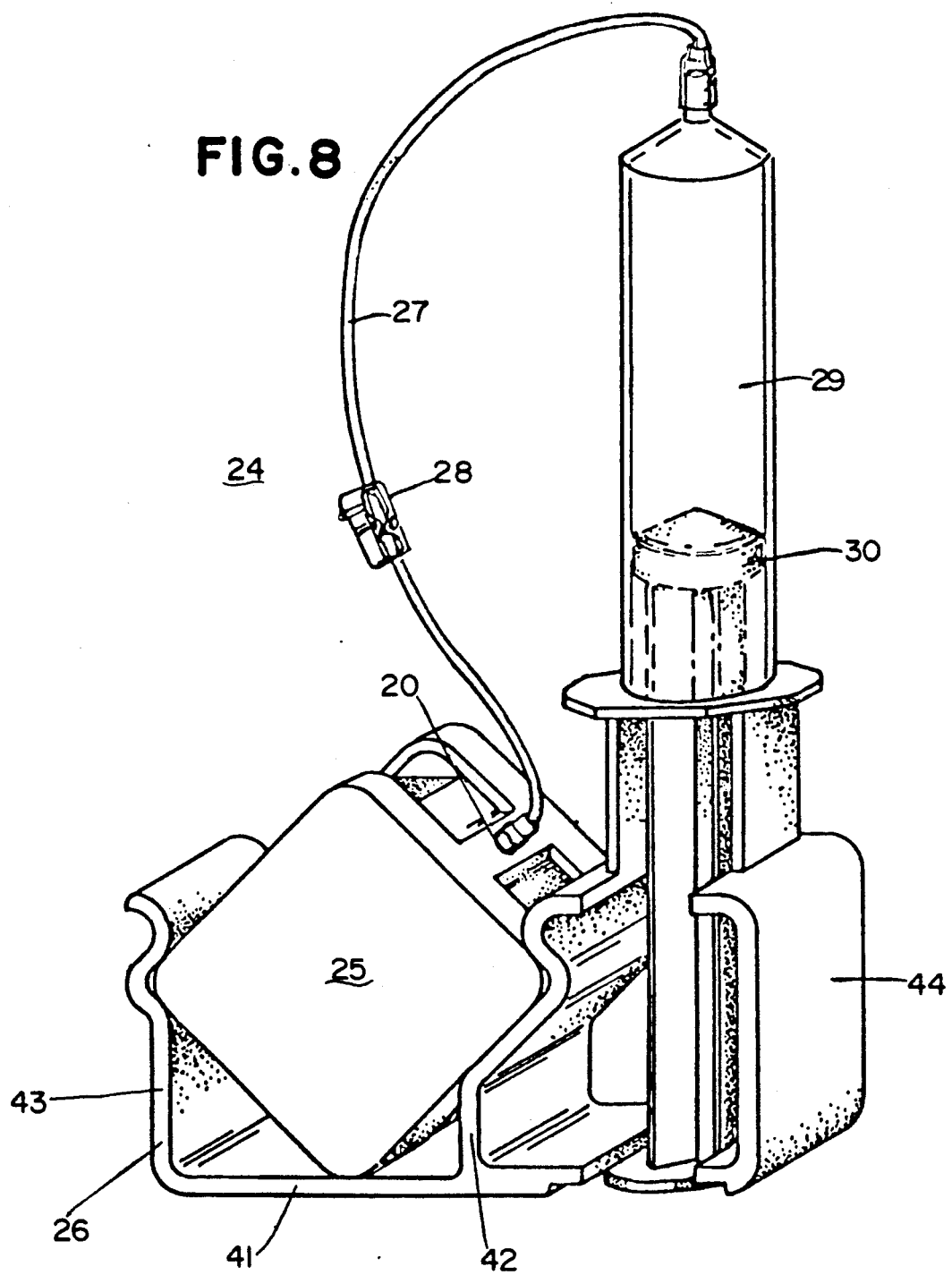
FIG. 8 is a schematic view of a preferred apparatus for use with the device of the invention.

Referring to FIG. 1 there is shown a concentrating device 40, according to one embodiment of the invention, comprising an outer enclosure 1, impermeable to sample solution, and a cover 2. Ports 3A and 3B in cover 2 allow for the introduction of sample solutions and the removal of liquid retentate. On the lower surface of enclosure 1, in opposing parallel relationship to cover 2, there is a second cover (not shown) identical to cover 2, also having two ports. A liquid tight seal is provided between covers 2 and enclosure 1, e.g. by bonding via the use of adhesives such as epoxides, by ultrasonic welding, heat sealing, etc.. Optionally, as shown in FIGS. 1 and 2, cover 2, which is impermeable to the sample solution ("impermeable"), has a ridge 4 disposed on its lower periphery, which mates with shoulder 5 of enclosure 1, as shown in the detail A (FIG. 2) to help provide the liquid tight seal between the cover and the enclosure. Disposed within enclosure 1, as shown in FIG. 4, are a pair of concentration units, each unit comprising a chamber 9, absorbent layer 8, and resilient layer 7. One wall (preferably rigid) of each chamber 9 is formed by the lower surface of cover 2, while the opposing wall of the chamber 9 is formed by a semipermeable membrane 6, which is permeable to the solvent in the sample solution to be concentrated ("permeable"), but impermeable to the macromolecules or other solutes which are to be retained. In the embodiment shown in FIGS. 1 and 2, the side walls of chamber 9 are formed by ridge 4, as shown in detail A. Semipermeable membranes 6 are sealed to the surface of frames 10 (one such frame 10 being shown in FIG. 3) forming regions in the membrane (10A, 10B, 10C and 10D) which are impermeable to the sample solution. It is preferred, but not necessary for purposes of the invention that the impermeable regions in the membrane be formed by sealing the membrane to a frame. Rather, regions of the membrane could be rendered impermeable by means such as painting, taping, etc. When a plurality of concentration units are disposed within the enclosure 1, e.g. two units as shown in FIG. 4, each concentration unit has a frame 10. The frame is preferably on the side of the membrane furthest from the sample chamber, such that the volume of the sample chamber is not reduced by its presence. However, it is possible to have the frame on the chamber side of the membrane, particularly if the frame is very thin. In the embodiment shown in FIG. 3, the frame 10 forms four approximately rectangular solvent impermeable membrane regions having different areas (10A, 10B, 10C and 10D). Frame 10 may be integral with the enclosure 1, or may be a separate sheet which is joined to the enclosure at its edges.

In the embodiment shown in FIG. 1, absorbent layer 7 serves to draw the solvent through the semipermeable membrane and retain it. Resilient layer 8 is situated in the concentration unit adjacent absorbent layer 7 such that it provides apposition between the absorbent layer 7 and its adjacent membrane 6, thus improving the flow of solvent through the membrane.

As seen in FIG. 4, the paired concentration units are separated by a wall 11, which is impermeable to the solvent of the sample solution and preferably rigid, and which, like frame 10, may be integral with the enclosure 1 or joined thereto. Wall 11 allows two sample solutions to be concentrated simultaneously, one in each concentration unit, without any cross-contamination. Preferably, the two frames 10 have the same orientation on both sides of the enclosure such that the two samples will have the same concentration; however the frames 10 may be oriented differently if desired, such that samples of different concentrations can be obtained from the two units. It is generally preferred to have two concentration units, as shown in FIG. 1 and described above, as it is standard practice to run analytical tests using duplicate samples. However, the concentrating device functions equally well with a single unit.

In the preferred embodiment shown in FIGS. 1-7, the resilient and absorbent layers have approximately the same dimensions (length and width) and fit within the interior of the frame, i.e. the portion of the membrane which is permeable to solvent has approximately the same dimensions as the resilient and absorbent layers. In general, it is preferred that the resilient layer have at least the length and width of the absorbent layer so that the entire absorbent layer is pressed evenly against the surface of the membrane. It is also preferred that the absorbent layer have at least the length and width of the solvent permeable area of the membrane so that the proper volume of solvent is drawn through the membrane. However, the absorbent layer and resilient layer may be larger than these requirements, if desired.

Frames 10 and wall 11 are disposed between and substantially perpendicular to the side walls of enclosure 1. In the case where only one concentration unit is desired, a bottom wall of enclosure 1 would obviously take the place of the second cover 2 such that the entire concentration unit would be enclosed. Enclosure 1 may be hollow or solid, e.g., if the resilient layers, absorbent layers and the area of the membrane which is permeable to solvent have approximately the same dimensions, the side walls o the enclosure may extend from the periphery of the membrane to the periphery of the absorbent and resilient layers (i.e. the exterior of frame 10 to the interior of frame 10) and thus be solid, or the side walls of the enclosure could just extend downward from the periphery of the membrane, leaving a space between the periphery of the absorbent and resilient layers and the enclosure side walls and thus be hollow. If the enclosure 1 is solid, the enclosure itself forms both wall 11 and frames 10. A hollow enclosure is generally preferred as it requires less material and is more economical. If the enclosure 1 is hollow, it is preferred that each resilient layer and adjacent absorbent layer be surrounded on each face, except the face of the absorbent layer adjacent to the membrane, by solvent impermeable walls, so that solvent is retained within the concentration unit. The enclosure 1, wall 11 and frames 10 are generally plastic, preferably polystyrene and copolymers thereof, e.g. styrene acrylonitrile, etc, but may be of any suitable material which is impermeable to the sample solution. It is preferred that at least the enclosure 1 and covers 2, and preferably also the frames 10 and wall 11 be transparent, such that the functioning of the device and the sample level within the chamber can be observed by the user. A preferred method of forming the enclosure, wall and frames is to mold them as a single integral part.

It is necessary to provide means for the introduction of sample solution to and the removal of concentrated liquid retentate from the chamber 9 such as at least one port disposed in cover 2. Ports 3A and 3B, as shown in FIGS. 1 and 3, provide such a means. Ports 3A and 3B allow introduction of sample solution to and removal of concentrated liquid retentate from the device by syringe or pipette, and are preferably of luer lock type, being provided with suitable removable caps. It is generally preferred that the retentate be removed by pipette when there is a small volume of highly concentrated retentate since more complete sample recovery is usually obtained by pipette than by syringe. When a syringe is used, it is preferable to use a blunt ended needle so that the membrane is not pierced upon introduction of the sample solution and so that recovery of the liquid retentate is made easier. It is preferred that chamber 9 have a venting means for air or other gases. If there are at least two ports disposed in cover 2 for the introduction of sample solution and removal of concentrated retentate, then one of said ports can be used as such a venting means.

The membrane 6 may be of any conventional construction and formed of cellulosic, polysulfone, or other polymeric material, being selected so as to be permeable to the solvent or solvents in the liquid sample solutions to be concentrated while at the same time being impermeable to the macromolecules or other solutes which are to be retained. The size of the solutes to be retained is a factor in selection of the membrane. Although the membrane can be of any type such as an ultrafiltration membrane, microfiltration membrane, etc., it is particularly preferred that the membrane be an anisotropic ultrafiltration membrane. The membranes 6 may be sealed to the surface of frames 10 by any suitable means such as cement, adhesive, solvent bonding, heat sealing or ultrasonic sealing. The preferred method will depend upon the specific membrane used.

The spacing between the membrane 6 and the lower surface of cover 2 is desirably kept small, on the order of 30 to 250 mils, in order to maximize the ratio of membrane surface to chamber volume while minimizing capillary forces which tend to restrain the passage of solvent through the membrane.

The absorbent layers 7 are formed of a material which readily absorbs the solvent of the sample solution to be concentrated and is readily wet by the solvent. If the solvent is water, the most commonly encountered solvent, the absorbent material is preferably hydrophilic. The absorbent layers may comprise small discrete particles or a powder of absorbent material such as silica gel or cross-linked dextran sold under the tradename Sephadex ®, or may be particles such as polyethylene glycol which not only absorb a solvent such as water but dissolve in it. However, for best results from the standpoint of stability during shipment and uniformity of results during use, it is generally preferred that the absorbent layers be in the form of coherent and self-supporting sheets of fibrous material which retain their shape and dimensions regardless of mechanical shocks to which the device may be subjected during shipment or use. Satisfactory results may be obtained using sheets of blotting paper or the like. The best controlled flow, in the case of sample solutions containing water as the solvent, may be obtained with sheets of purified cellulose fibers which are thick enough so that they are capable of absorbing the desired volume of solvent. In the case of a device in which the sample chambers are approximately 2 mm in thickness, excellent results may be obtained using fibrous absorbent sheets approximately 10-20 mm in thickness.

For maximum speed of removal of solvent through the membrane, it is important that the spacing between each membrane and the corresponding absorbent layer be as small as possible. Consequently, the surface of the absorbent layer is preferably very smooth. Small irregularities or roughness of the surface of the absorbent layer can be smoothed out by employing one or more layers of smooth thin tissue paper as a supplemental fibrous water absorbent layer between the absorbent layer and the membrane.

The resilient layer is generally formed of polyurethane sponge, but may be of any suitable resilient material such as natural or synthetic rubbers, etc. The resilient layer provides apposition between the absorbent layer and the corresponding membrane. The layer of resilient material, when compressed in the assembled device, serves to press the absorbent layer against the membrane, thereby accomodating any irregularities in the surface of the layers and enhancing flow through the membrane. The resilient layer may but does not generally serve to absorb or retain the solvent, as the capacity of the absorbent layer is usually adequate to retain all of the solvent. The thickness of the resilient layer is not critical, provided it can provide adequate apposition between the absorbent layer and the corresponding membrane. Although not required, in the embodiment shown in FIG. 4, the resilient layer is thinner than the absorbent layer. In fact, as described hereinabove, this resilient layer is optional, since apposition may be provided simply by compressing a compressible absorbent layer.

To concentrate a sample solution, e.g. a solution containing macromolecules, the concentrating device 40 is placed such that the covers 2 are substantially vertical and the device rests on one of the sides of the enclosure as seen in FIG. 3. The side on which the device rests when in use will determine the level of concentration. Alternatively, the device may be placed on one of the edges of enclosure 1 as shown in FIG. 8, in order to obtain concentrations intermediate the two concentrations obtained when the device is used resting on the sides immediately adjacent that edge. The sample is introduced to the device through one of the ports 3A or 3B (either the upper or lower may be used), while the other is left slightly open to allow air to escape from the chamber 9. As the sample solution fills the chamber 9, the solvent is drawn through the unsealed (solvent permeable) areas of membrane 6 by the absorbent layer 7. The resulting filtrate is retained within the absorbent layer. A vacuum may be applied to the concentration unit to aid in the drawing of solvent through the solvent permeable areas of membrane 6, and to increase the rate of filtration through the membrane. In fact, it is even possible to eliminate the absorbent and resilient layers of the concentration unit and replace them simply with a membrane support and a means, such as a vacuum, for drawing the solvent through the solvent permeable areas of the membrane. In this embodiment, it is important that the vacuum be relatively weak, such as $-50$ to $-100$ mm Hg, so that the macromolecules or other solutes in the sample solution are not trapped in the membrane structure due to the force of the vacuum. The filtering of solvent through the solvent permeable areas of membrane 6 continues until the liquid level in chamber 9 is at the upper margin of the sealed (solvent impermeable) region adjacent to the side of the enclosure on which the device rests, a process which generally requires from thirty minutes to two hours. Accordingly, the concentrated liquid retentate is retained in a retaining well, the volume of which retaining well is defined by said solvent impermeable area, the cover 2, and the side walls of chamber 9. When the level of the sample solution has been lowered to the upper margin of the sealed (solvent impermeable) region, filtration stops automatically, leaving a precisely predetermined quantity of concentrated macromolecular liquid retentate in the retaining well for removal at the convenience of the operator.

Obviously, there are the same number of retaining wells as there are solvent impermeable regions of membrane 6. The volume of concentrated liquid retentate retained in a retaining well of chamber 9 is directly proportional to the area of the solvent impermeable region, and the concentration of the macromolecules or other solutes is inversely proportional to the final volume of the concentrated retentate; i.e. a larger sealed (solvent impermeable) region produces a larger volume, resulting in a more dilute retentate. For example, if device 40 were positioned as shown in FIG. 3, the retentate retained in the retaining well would have the greatest concentration of solutes possible with the device shown, since the solvent impermeable region of membrane 6 adjacent the bottom surface of the enclosure (impermeable region 10C) has the smallest area of the four impermeable membrane regions 10A, 10B, 10C and 10D.

After concentration, the retentate may be withdrawn through the lower port (e.g. port 3A in FIG. 3). This may be accomplished by removing the luer lock cap and draining the retentate, or by withdrawing the retentate from the port by syringe.

An alternate embodiment of the invention is shown in FIGS. 5-7. This embodiment differs from the embodiment described above, and shown in FIGS. 1-4, primarily in the shape of the inner periphery of the frame, and thus the configuration of the solvent impermeable regions of the membrane. Although both the embodiment of FIGS. 1-4 and the embodiment of FIGS. 5-7 provide precise and efficient concentration of solutes such as macromolecules, the configuration shown in FIGS. 5-7 is generally preferred. For instance, in the case where the retentate is highly concentrated, e.g. the volume of retentate is small, it is easier to recover retentate from a triangular retaining well (e.g. 16A, C and D in FIG. 5) than from a rectangular retaining well (e.g. 10A-10D in FIG. 3). Also, when a rectangular retaining well is very narrow, as 10C in FIG. 3, filtration to dryness may occur. Where a highly concentrated retentate is desired, this possible problem of filtration to dryness may be eliminated by the use of a triangular retaining well.

The shape of the inner periphery of frame 16 differs from that of frame 10 of FIGS. 1-4. While the membranes of both the embodiments shown in FIGS. 1-4 and FIGS. 5-7 are approximately square or rectangular (this is preferred, but not a requirement), frame 10 provides four approximately rectangular solvent impermeable membrane regions having different areas which are situated such that each rectangular impermeable region extends lengthwise along one of the four sides of the membrane at the periphery of the membrane, whereas frame 16 provides an approximately triangular solvent impermeable membrane region for each of three corners of the membrane (16A, C and D), and a fourth approximately rectangular solvent impermeable membrane region (16B) which extends lengthwise along one side of the membrane at the periphery of the membrane. In a variation of this embodiment, the frame may provide four approximately triangular solvent impermeable (sealed areas, one at each of the four corners, or any other combination of rectangular and triangular sealed areas. However, it has been found that the square configuration of FIGS. 5–7 having three triangular impermeable regions and one rectangular impermeable region is convenient when the device is to provide the four concentrations which are most often used, i.e. $5\times$, $10\times$, $25\times$ and $50\times$, since, in some cases, it may be uneconomical to manufacture the absorbent layer in a configuration to fit within four triangular sealed areas.

The resilient layer 19, absorbent layer 18, membrane 17 and chamber 21 in this embodiment are generally the same as the corresponding elements described in reference to FIGS. 1–4. There are again two concentration units, separated by separating wall 23, which wall 23 may be integral with or joined to enclosure 15, and two covers 13 which mate with enclosure 15. In this embodiment, covers 13 have walls which mate on their inner surface with ridges 14 on the enclosure. Each cover has four ports, 22A–D, which allow for the introduction of sample solution and withdrawal of concentrated liquid retentate, preferably by pipette in order to maximize sample recovery. In this embodiment, the sample may be introduced, and concentrated liquid retentate withdrawn, through any of the ports. When the device is used in the position shown in FIG. 8, retentate is preferably withdrawn through the port which is directly above the retaining well of the chamber 21 in which the concentrated retentate is retained so that the device need not be removed from the apparatus (i.e. retentate which is in the retaining well defined by impermeable membrane area 16B is withdrawn through port 22B, 16C through 22C, etc.). The retentate may also be withdrawn through the port below the retaining well in which it is retained if so desired, e.g. when the retentate is highly concentrated. Two vacuum ports 20 are also provided, through which a vacuum may be applied to each concentration unit.

It is not necessary that the frame and thus the solvent impermeable membrane regions, have either of the configurations described above. The only requirement is that two or more solvent impermeable regions be formed in the membrane such that, when the device is placed in two or more positions, different desired retentate concentrations will be obtained.

FIG. 8 is a schematic drawing of an apparatus 24 which may be used with a device of the invention, which apparatus 24 comprises a retaining means 26 which comprises base 41 and a means for releasably securing the device to the base such that the device rests on the base and is retained in a desired position. The means for releasably securing the device to base 41 preferably comprises at least two arm members extending from the base, e.g. substantially vertical members 42 and 43, situated such that the device is disposed between the arm members. It should be noted that in FIG. 8 a device 25 according to the invention, is shown resting on one of the edges of the enclosure. This is the orientation generally used with the device shown in FIGS. 5–7. The concentrating device shown in FIGS. 1–4 is generally used resting on one of the sides of enclosure 1, however alternatively it may be used resting on any of the edges of the enclosure as previously described. Apparatus 24 is particularly adapted to hold the device in either orientation, and allows the operator to easily clip the device in the desired orientation by displacing one of the arm members, which are preferably at least slightly flexible.

A syringe 29, with plunger 30, also fits into the retaining means 26, disposed between substantially vertical members 42 and 44. The tip of syringe 29 is connected by tubing 27 to a single vacuum port 20 of the device, with a clamping means 28 disposed between the syringe and the vacuum port. Rather than using two vacuum ports 20, as shown in FIG. 5, the single vacuum port 20 shown divides into two passages, each of which communicates with one of the two concentration units. A weak vacuum may be applied to the device through the vacuum port by pulling back on plunger 30, thereby evacuating the body of the syringe.

While preferred embodiments have been described hereinabove, it is to be understood that many variations and modifications may be made by those skilled in the art without departing from the scope and spirit of invention.

What is claimed is:

1. A filtration device for removing solvent from a solute-containing sample solution to obtain a desired final retentate concentration comprising at least one concentration unit, each said concentration unit comprising:
    a) one or more chambers, each chamber comprising at least one chamber wall impermeable to sample solution; and at least one wall, which wall is in opposing spaced relation to said impermeable chamber wall, and which wall is formed of a semipermeable membrane permeable to said solvent and impermeable to the solute to be retained, said membrane having at least two regions of different area, which regions are impermeable to said solvent, each of said regions providing a deadstop preventing filtration to dryness of the solvent through the membrane and providing a different final retentate concentration; and
    b) means for drawing said solvent through said membrane.

2. The device of claim 1 wherein the solute comprises macromolecules.

3. The device of claim 2 wherein the membrane comprises an anisotropic ultrafiltration membrane.

4. The device of claim 1 wherein the means for drawing solvent through the membrane comprises at least one absorbent layer disposed closely adjacent the side of the membrane furthest from the chamber.

5. The device of claim 4 further comprising means for providing apposition between each said absorbent layer and its adjacent membrane.

6. The device of claim 5 wherein said apposition providing means comprises a layer of resilient material disposed adjacent each said absorbent layer.

7. The device of claim 6 comprising a means for retaining each resilient layer adjacent each absorbent layer and wherein said retaining means serves to compress the resilient layer such that the absorbent layer is pressed against the membrane.

8. The device of claim 6 wherein the resilient layer, the absorbent layer and the portion of the membrane which is permeable to solvent have approximately the same dimensions.

9. The device of claim 8 wherein said membrane is approximately square or rectangular, and there are four approximately rectangular solvent permeable membrane regions having different areas which are situated such that each rectangular solvent impermeable membrane region extends lengthwise along one of the four sides of the membrane at the periphery of the membrane.

10. The device of claim 8 wherein the membrane is approximately square or rectangular and there is an approximately triangular solvent impermeable membrane region at each of three of the four corners of the membrane and a fourth solvent impermeable membrane region which is approximately rectangular and which extends lengthwise along one side of the membrane at the periphery of the membrane.

11. The device of claim 6 wherein each said resilient layer and adjacent absorbent layer is surrounded on each face, except the face of the absorbent layer adjacent to the membrane, by solvent impermeable walls.

12. The device of claim 5 wherein the means for drawing solvent through the membrane further comprises a vacuum means.

13. The device of claim 4 wherein said absorbent layer comprises a sheet of fibrous material.

14. The device of claim 13 wherein said fibrous material comprises a sheet of cellulose fibers.

15. The device of claim 1 further comprising a support for the membrane and wherein the means for drawing solvent through the membrane comprises a vacuum means.

16. The device of claim 1 wherein the permeable chamber wall is transparent.

17. The device of claim 1 further comprising an enclosure for the at least one concentration unit, said enclosure being impermeable to the sample solution.

18. The device of claim 17 wherein the enclosure is transparent.

19. The device of claim 1 comprising two concentration units.

20. The device of claim 19 wherein the two concentration units have their membrane walls in opposing spaced relation, and the concentration units are separated by at least one separating wall impermeable to the sample solution.

21. The device of claim 1 wherein the solvent impermeable regions of the membrane are rendered solvent impermeable by sealing said membrane regions to the surface of a frame.

22. The device of claim 21 further comprising an enclosure for the at least one concentration unit, said enclosure being impermeable to the sample solution.

23. The device of claim 22 wherein said frame is integral with the enclosure.

24. The device of claim 21 wherein the frame is plastic.

25. The device of claim 1 wherein the membrane regions which are impermeable to the solvent have approximately rectangular shape.

26. The device of claim 1 wherein said membrane is approximately square or rectangular, and there are four approximately rectangular solvent impermeable membrane regions having different areas which are situated such that each rectangular solvent impermeable membrane region extends lengthwise along one of the four sides of the membrane at the periphery of the membrane.

27. The device of claim 1 wherein the membrane is approximately square or rectangular and there is an approximately triangular solvent impermeable membrane region at each of three of the four corners of the membrane and a fourth solvent impermeable membrane region which is approximately rectangular and which extends lengthwise along one side of the membrane at the periphery of the membrane.

28. The device of claim 1 wherein the membrane is approximately square or rectangular and there is an approximately triangular solvent impermeable membrane region at each of the four corners of the membrane.

29. The device of claim 1 wherein the chamber further comprises venting means.

30. The device of claim 1 further comprising means for introducing sample solution to the chamber and for removing concentrated liquid retentate from the chamber.

31. The device of claim 30 comprising one or more ports disposed in the chamber wall 32. The device of claim 29 further comprising means for introducing sample solution to the chamber and for removing concentrated liquid retentate from the chamber.

33. The device of claim 32 comprising two or more ports disposed in the chamber wall.

34. The device of claim 29 wherein the venting means comprises a port in the chamber wall.

35. The device of claim 1 wherein the chamber further comprises side walls which support each membrane in opposing relation to the chamber wall.

36. An apparatus for retaining a device of claim 1 comprising a base and means for releasably securing the device to the base such that the device rests on the base and is retained in a desired position.

37. The apparatus of claim 36 wherein the means for releasably securing the device to the base comprises at least two arm members, extending from the base, situated such that the device is disposed between the arm members.

38. The apparatus of claim 36 further comprising a vacuum means which is secured to said apparatus and attached to said device.

39. A filtration device for removing solvent from a solute-containing sample solution to obtain a desired final retentate concentration comprising at least one concentration unit, each said concentration unit comprising:
a) one or more chambers, each chamber comprising:
  i) at least one chamber wall impermeable to sample solution;
  ii) at least one wall, which wall is in opposing spaced relation to said impermeable chamber wall and which wall is formed of a semipermeable membrane permeable to said solvent and impermeable to the solute to be retained, said membrane having at least two regions of different area, which regions are impermeable to said solvent, each of said regions providing a dead-stop preventing filtration to dryness of the solvent through the membrane and providing a different final retentate concentration;
  iii) side walls which support each membrane in opposing spaced relation to the chamber wall;

b) at least one absorbent layer disposed closely adjacent the side of the membrane furthest from the chamber;
c) at least one layer of resilient material disposed adjacent said absorbent layer and providing apposition between said absorbent layer and its adjacent membrane;
d) means for introducing sample solution to the chamber;
e) means for removing concentrated liquid retentate from the chamber; and
f) an enclosure for the at least one concentration unit, said enclosure being impermeable to the sample solution.

40. The device of claim 39 wherein the solute comprises macromolecules and the semipermeable membrane comprises an ultrafiltration membrane.

41. A method obtaining a final retentate having a desired concentration comprising the steps of:
a) introducing a solute-containing sample to be concentrated to a chamber of a device comprising:
i) one or more chambers, each chamber comprising at least one chamber wall impermeable to sample solution; and at least one wall, which wall is in opposing spaced relation to said impermeable chamber wall, and which wall is formed of a semipermeable membrane permeable to said solvent and impermeable to the solute to be retained, said membrane having at least two regions of different area, which regions are impermeable to said solvent, each of said regions providing a deadstop preventing filtration to dryness of the solvent through the membrane and providing a different final retentate concentration; and
ii) means for drawing said solvent through said membrane; and
b) obtaining a predetermined quantity of solute concentrated liquid retentate by drawing solvent through the membrane until the liquid level in the chamber is at the upper margin of one of the solvent impermeable membrane regions and filtration stops.

42. The method of claim 41 further comprising the step of: c) withdrawing the concentrated final retentate from the chamber.

43. The method of claim 41 wherein the solute comprises macromolecules and the semipermeable membrane comprises an ultrafiltration membrane.

* * * * *